United States Patent [19]

Bader

[11] Patent Number: 5,846,206
[45] Date of Patent: Dec. 8, 1998

[54] METHOD AND APPARATUS FOR MONITORING AND ESTIMATING THE AWAKENESS OF A PERSON

[75] Inventor: Gaby Bader, Gothenburg, Sweden

[73] Assignee: Biosys AB, Gothenburg, Sweden

[21] Appl. No.: 750,452

[22] PCT Filed: Jun. 1, 1995

[86] PCT No.: PCT/SE95/00629

§ 371 Date: Jan. 7, 1997

§ 102(e) Date: Jan. 7, 1997

[87] PCT Pub. No.: WO95/33403

PCT Pub. Date: Dec. 14, 1995

[30] Foreign Application Priority Data

Jun. 7, 1994 [SE] Sweden .................................. 9401959

[51] Int. Cl.⁶ .......................... A61B 5/0205; A61B 5/02
[52] U.S. Cl. .......................... 600/534; 600/527; 600/513
[58] Field of Search .......................... 600/372, 382, 600/513, 527, 529, 534, 552, 553

[56] References Cited

U.S. PATENT DOCUMENTS

| | | |
|---|---|---|
| 4,732,157 | 3/1988 | Kaplan et al. .................. 600/508 |
| 5,101,831 | 4/1992 | Koyama et al. . |
| 5,187,657 | 2/1993 | Forbes . |
| 5,448,996 | 9/1995 | Bellin et al. . |
| 5,479,932 | 1/1996 | Higgins et al. .................. 600/529 |
| 5,622,178 | 4/1997 | Gilham . |
| 5,671,733 | 9/1997 | Raviv et al. . |

*Primary Examiner*—William E. Kamm
*Assistant Examiner*—Carl H. Layno
*Attorney, Agent, or Firm*—Young & Thompson

[57] ABSTRACT

For monitoring and estimating a person's wakefulness, a stationary pressure sensor contacts part of that person's body and generates a signal corresponding to that person's body movements relative to the sensor. A detector/filter circuit connected to the sensor separates signals corresponding to true body movements, heartbeat-related body movements, and respiration-related body movements. Calculation and comparison circuits are adapted to receive these signals and compare them with previously received signals to determine possible changes. A correlator correlates the output signals from the calculation and comparison circuits to produce a resulting change signal which is compared with a preset wakefulness threshold in a threshold detector circuit. An alarm device is triggered, when the preset threshold is reached as an indication of a reduced degree of wakefulness.

14 Claims, 3 Drawing Sheets

1

METHOD AND APPARATUS FOR MONITORING AND ESTIMATING THE AWAKENESS OF A PERSON

TECHNICAL FIELD

The invention relates to a method and an apparatus for monitoring and estimating a person's wakefulness and, thereby, drowsiness.

BACKGROUND OF THE INVENTION

It is known, e.g. from the article "Determination of sleep state in infants using respiratory variability", PEDIATR. RES. 1987, Haddad, GG, JENG, HJ, LAI, TL, MELLINS RB., that in connection with cardiac/respiratory research on infants, changes in the cardiac/respiratory activity at short, instantaneous (REM/Rapid Eye Movement) sleep differ from a corresponding changes at calm, deep sleep.

BRIEF DESCRIPTION OF THE INVENTION

The object of the present invention is to utilize a corresponding relationship between the cardiac/respiratory function and a person's body movements in order to estimate the person's wakefulness and, thereby, the drowsiness of the person in question.

This is attained by means of the method according to the invention in that an electric signal is generated in response to said person's body movements relative to at least one stationary pressure sensitive means which contacts at least a portion of said person's body, that signals are separated from said electric signal in correspondence to the duration and magnitude of true body movements, the amplitude of heartbeat-related body movements as a function of rate, and the amplitude of respiration-related body movements as a function of rate, that the duration and magnitude of said true body movements as well as the time-interval between same are measured and compared with previously measured corresponding values to determine possible changes, that the amplitude of every heartbeat-related and every respiration-related body movement as well as the time-interval between at least two successive heartbeats and respirations, are measured and compared with previously measured corresponding values to determine possible changes, that heartbeat-related and respiration-related changes are correlated with true body movement changes, that the resulting change is compared with a preset wakefulness threshold and that an alarm is triggered when the threshold is reached as an indication of a reduced degree of wakefulness.

The object is also attained by means of the apparatus according to the invention, which comprises at least one stationary pressure sensitive means which is adapted to contact at least a portion of said person's body, and to generate an electric signal on its output terminal in response to said person's body movements relative to same, a detector/filter circuit, connected to the output terminal of said at least one stationary pressure sensitive means, and adapted to separate, from said electric signal, signals corresponding to the duration and magnitude of true body movements, to the amplitude of heartbeat-

2 related body movements as a function of rate, and to the amplitude of respiration-related body movements as a function of rate, and output these separated signals on corresponding output terminals, a first calculation and comparison circuit which is adapted to receive, on its input terminal, said signal corresponding to true body movements, to calculate the duration and magnitude of the true body movements as well as the time interval between same, and to compare these calculated values with previously calculated corresponding values to determine possible changes, a second and a third calculation and comparison circuit which are adapted to receive, on their input terminals, said signal corresponding to heartbeat-related and respiration-related body movements, respectively, to calculate the amplitude of every heartbeat-related and every respiration-related body movement, respectively, as well as the time interval between at least two successive heartbeats and respirations, respectively, and to compare these calculated values with previously calculated corresponding values to determine possible changes, a correlator, connected to the the output terminals of said three calculation and comparison circuits, and adapted to correlate heartbeat-related and respiration-related changes with true body movement changes, a threshold detector circuit, connected to the output terminal of the correlator, and adapted to compare the resulting change with a preset wakefulness threshold, and an alarm device, connected to the output terminal of the threshold detector circuit, and adapted to trigger alarm when the preset threshold is reached as an indication of a reduced degree of wakefulness.

The advantage of the invention is that, by means of the method and the apparatus according to the invention, it is possible, in an efficient manner, to monitor the degree of wakefulness of e.g. drivers of different types of vehicles (cars/buses/trains/boats/aircrafts) without disturbing the monitored person in that also the body movements of the monitored person are taken into account. Other suitable groups to monitor may be persons having a sedentary occupation such as students, guards, operators in process plants, nuclear power plants, etc.

Moreover, the invention can be applied when studying syndromes characterized by state-dependent changes in heart and respiratory rate, such as sleep apnea or autonomic neuropathy.

Of course, it is also possible to apply the invention to other types of analyses aiming at establishing the state of wakefulness within different occupational groups or at different illnesses or other types of sleep disturbances.

BRIEF DESCRIPTION OF THE DRAWING

The invention will be described below in connection with an embodiment with reference to the appended drawing on which

PREFERRED EMBODIMENT

The invention is based on an investigation of a number of adults in a sleep laboratory using paper polysomnography and an equipment marketed under the trademark "Sleep-Box".

Different sleep stages were determined in accordance with classic neurophysiologic criteria. Cardiac R—R intervals, i.e. the time intervals between two heartbeats, and respiratory intervals as well as the amplitude of the waves were measured both manually and by means of wave detectors in epochs of 30–60 s. The intervals were determined over 15 minute periods for each sleep/wakefulness stage. It is of course also possible to determine the intervals continuously which is done in connection, e.g., with computer analysis. State-dependent beat-to-beat patterns were studied by plotting each R—R and respiratory interval against the previous interval. The results showed the highest beat-to-beat and respiratory variability during wakefulness and a large dispersion during REM with a progressive decrease during sleep, related to the sleep level. The smallest variations were attained on deep sleep.

In view of these results, a decision rule was developed for classifying different sleep stages according to the cardiac R—R and respiratory variability. This rule has been tested on normal healthy adults and the results show that more than 80% of the epochs are classified correctly.

Figure 1:
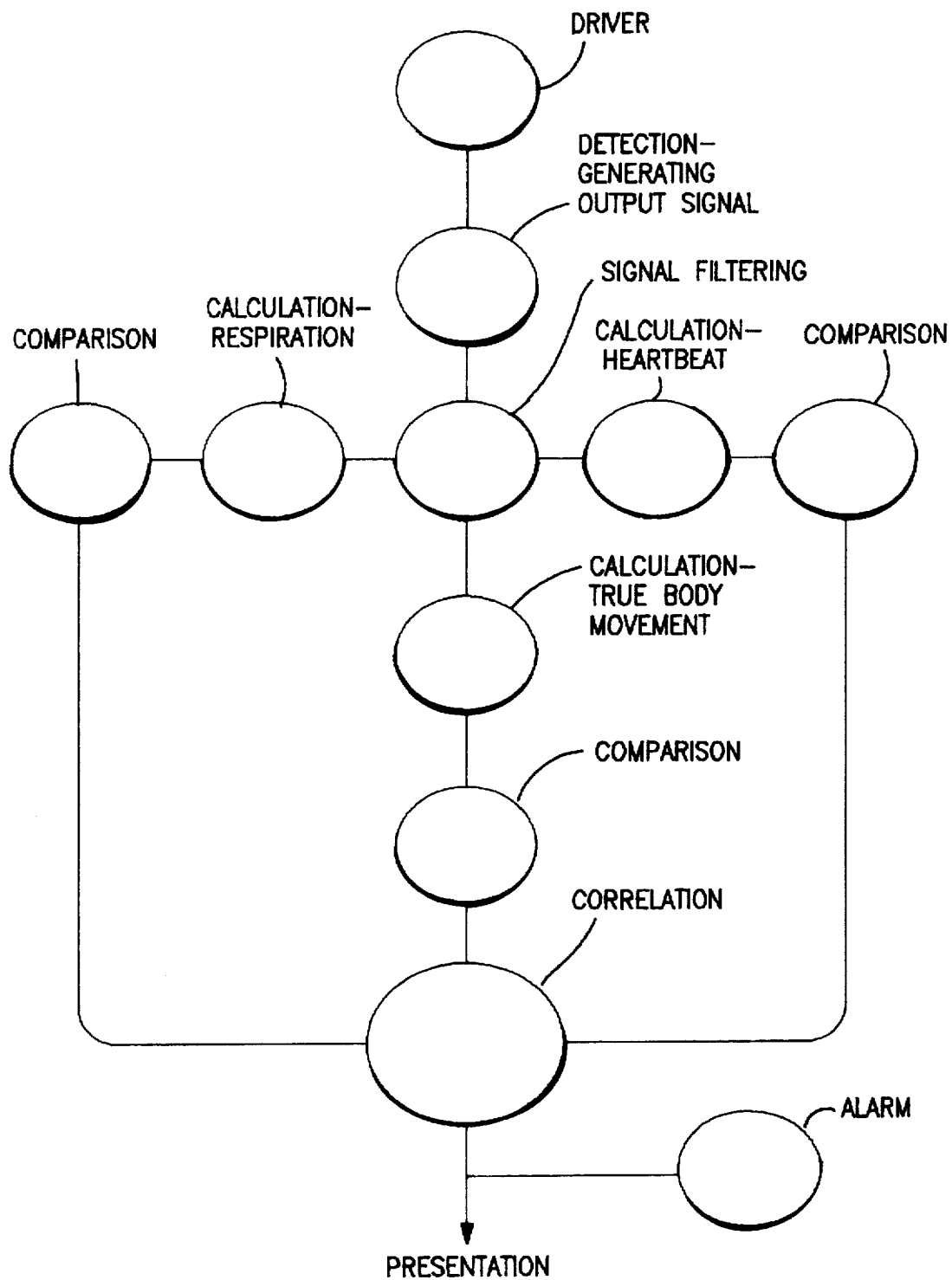
FIG. 1 shows a flow chart of the method according to the invention.

A process in accordance with the method according to the invention is described below with reference to FIG. 1. The described method is normally implemented by means of software. A person is sitting and driving, e.g., a car or another vehicle. Pressure sensitive, stationary plates or sensors are installed in the seat or the back of the seat and where appropriate possibly in a safety belt. The plates can be PVDF films possibly in combination with electrostatic plates. The driver's body movements cause different pressures against the plates which continuously register the pressure and the movements.

In a manner known per se, the plates generate electrical output signals which are detected and analyzed. Besides movements of the body, also the cardiac function and the respiratory function can be detected by means of these output signals. The amplitude and rate of the cardiac function are detected as are the amplitude and rate of the respiratory function. Depending on the driver's degree of wakefulness, the magnitude of these parameters varies. The signals are now to be analyzed and can either be analyzed directly or be stored in a memory for later transmission or be transferred simultaneously by wireless communication to a personal computer for storing and further processing of data. Analysis and processing of the signals take place continuously in a system which is designed for the purpose and coupled to the plates via wires or wirelessly connected to the plates, in which system each signal is analyzed independently of the other signals. The rate and amplitude of each heartbeat-related or respiration-related body movement, are calculated. The time intervals between two successive signals, are measured. Upon registering true body movements, the duration of the movements as well as the magnitude of the movements, are measured. Moreover, the time interval between movements is measured. The body movements are classified in accordance with duration and magnitude.

Moreover, in the system, the variations in time interval, amplitude and rate for each heartbeat and respiration, are compared with corresponding values for previous or successive heartbeats and respirations. Respiration and heartbeat changes are correlated with body movement changes. In order to obtain further information, it is also possible to register the pressure of the person's head against a head rest, if any.

By statistical analysis including i.a. multiple regression, it can be shown that there is a direct relationship between said parameters and changes in the person's degree of wakefulness. The system continuously compares processed data with the previously obtained standard material. Upon a reduced degree of wakefulness an alarm is triggered at a certain threshold level, which alarm can be an audio signal and/or a light signal.

Analysis and processing of data are carried out by means of a computer system controlled by an analysis program. When needed, the program reconstructs all signals which can then be presented on a screen (not shown) connected to the system. Also, the final result can be presented in the form of histograms or statistic tables.

FIGS. 2a–f show the variation when measuring cardiac R—R in relation to the previous interval in different stages of sleep/wakefulness.

Figure 2C:
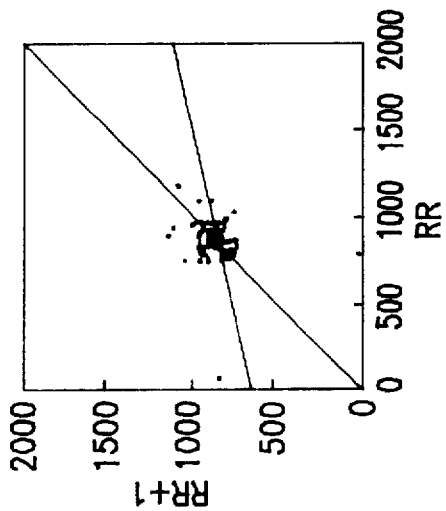
FIGS. 2a–f are diagrams of variations of cardiac R—R at different sleep stages.
Figure 2B:
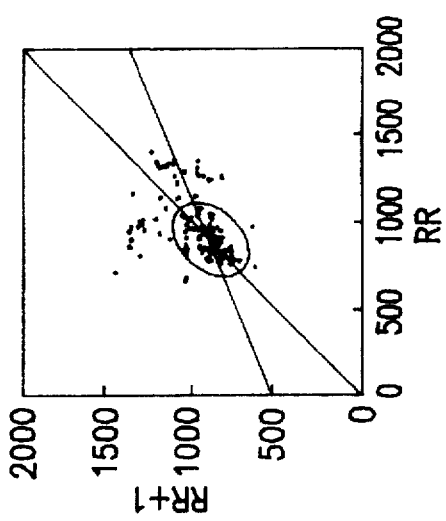
Figure 2A:
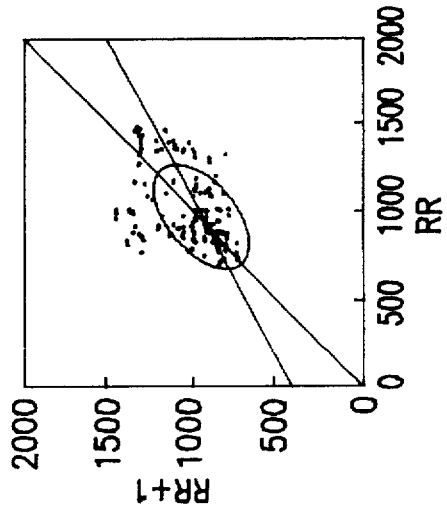
Figure 2F:
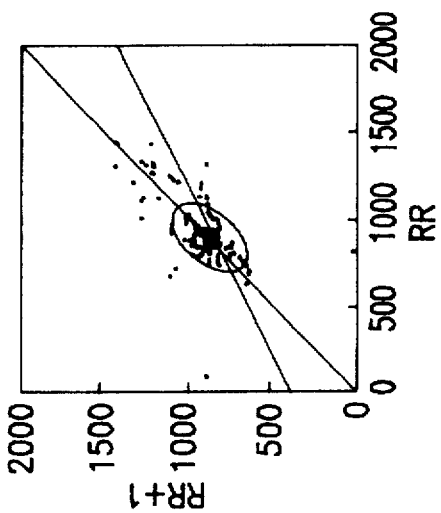
Figure 2E:
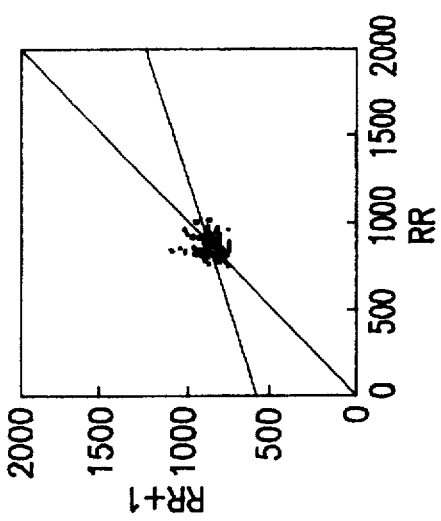
Figure 2D:
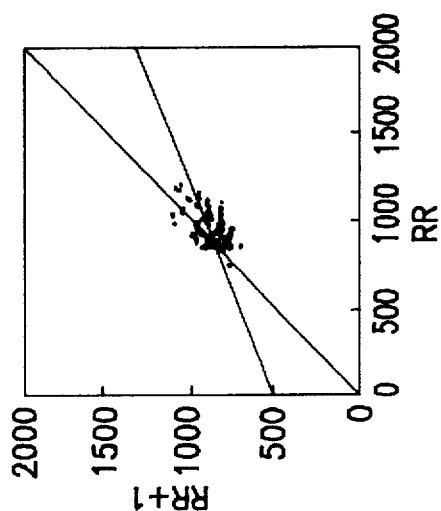

From FIG. 2a it is apparent that the variation is largest when awake. FIG. 2b shows the variation during REM, while FIGS. 2c–e show the variation at different sleep stages. As apparent, the variation decreases with deeper sleep. FIG. 2f shows that the variation increases at the reawakening. The horizontal axis indicates RR, i.e. the value actually measured. The vertical axis indicates RR+1, i.e. the value measured in the preceding interval.

Figure 3:
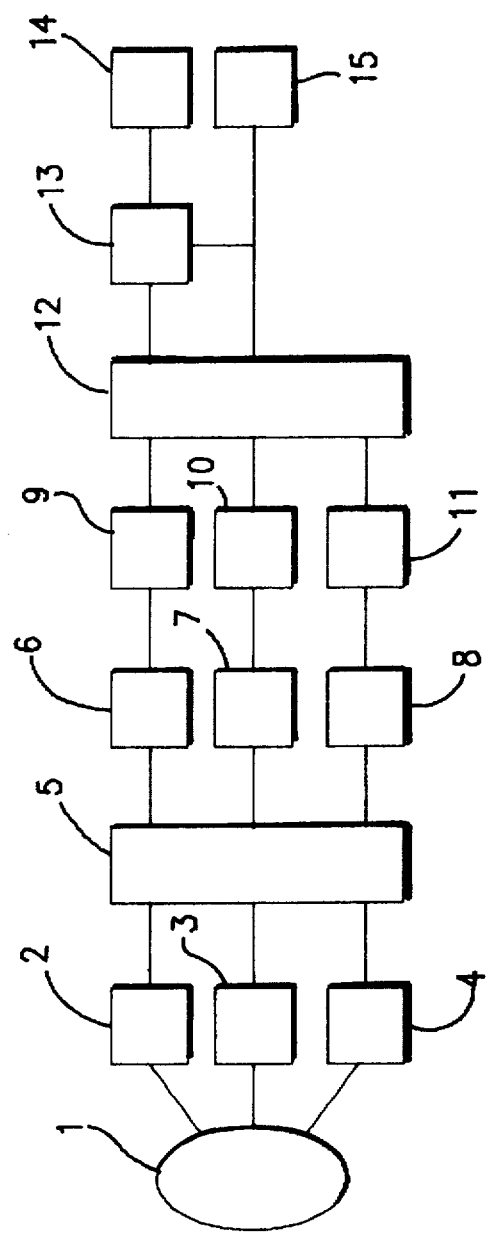
FIG. 3 shows a block diagram of an embodiment of an apparatus according to the invention.

In FIG. 3, in the form of a block diagram, an embodiment of an apparatus according to the invention, is shown. The embodiment relates to monitoring a driver 1 of a vehicle. As mentioned above, the driver 1 is in contact with pressure sensitive plates 2–4, which detect the driver's 1 body movements. The plates 2–4 generate output signals which are detected and filtered in respect of signal type in a detector/filter circuit 5. The different signal types are those corresponding to true body movements, heartbeat-related body movements and respiration-related body movements. From output terminals on the filter circuit 5, the signals are supplied to input terminals of calculation circuits 6–8 for calculation, in the circuit 6, of rate and amplitude for each heartbeat as well as the time interval between the heart beats, in the circuit 7, of rate and amplitude for each respiration as well as the time interval between the respirations, and, in the circuit 8, of the duration and magnitude of a true body movement as well as the time interval between true body movements. Comparison circuits (comparators) 9–11 receive on their input terminals, output signals from the circuits 6–8 and compare for each function, i.e. heart-related body movements, respiration-related body movements, and true body movements, the time interval variation, the variation in amplitude for heartbeat-related body movements and respiration-related body movements, respectively, with corresponding values for previously registered heartbeats and respirations, respectively, stored in memory means not shown.

A corresponding comparison is done in the circuit 11 for the duration, magnitude and variation of time intervals for true body movements. Thus, the output signals from the circuits 9–11 are controlled by said parameters and are supplied to input terminals of a correlator 12 in which heartbeat-related changes, respiration-related changes and true body movement changes are correlated. Since a direct relationship exists between the parameters and the degree of wakefulness, the parameter values will change upon e.g. a reduced degree of wakefulness. By means of a threshold detector circuit 13, such a threshold for the degree of wakefulness can be preset, at which an alarm is triggered, which activates an alarm device 14 in the form of e.g. an alarm bell or an alarm lamp or both, if suitable. 15 designates a visual presentation device, e.g. a screen.

I claim:

1. An apparatus for monitoring and estimating a person's wakefulness and, thereby, drowsiness, comprising at least one stationary pressure sensitive means (2, 3, 4) which is adapted to contact at least a portion of said person's (1) body, and to generate an electric signal on its output terminal in response to said person's body movements relative to same, a detector/filter circuit (5), connected to the output terminal of said at least one stationary pressure sensitive means (2, 3, 4), and adapted to separate, from said electric signal, signals corresponding to the duration and magnitude of true body movements, to the amplitude of heartbeat-related body movements as a function of rate, and to the amplitude of respiration-related body movements as a function of rate, and output these separated signals on corresponding output terminals, a first calculation and comparison circuit (8, 11) which is adapted to receive, on its input terminal, said signal corresponding to true body movements, to calculate the duration and magnitude of the true body movements as well as the time interval between same, and to compare these calculated values with previously calculated corresponding values to determine possible changes, a second and a third calculation and comparison circuit (6, 9 and 7, 10, respectively) which are adapted to receive, on their input terminals, said signal corresponding to heartbeat-related and respiration-related body movements, respectively, to calculate the amplitude of every heartbeat-related and every respiration-related body movement, respectively, as well as the time interval between at least two successive heartbeats and respirations, respectively, and to compare these calculated values with previously calculated corresponding values to determine possible changes, a correlator (12), connected to the the output terminals of said three calculation and comparison circuits (6, 9; 7, 10; 8, 11), and adapted to correlate heartbeat-related and respiration-related changes with true body movement changes, a threshold detector circuit (13), connected to the output terminal of the correlator (12), and adapted to compare the resulting change with a preset wakefulness threshold, and an alarm device (14), connected to the output terminal of the threshold detector circuit (13), and adapted to trigger alarm when the preset threshold is reached as an indication of a reduced degree of wakefulness.

2. Apparatus according to claim 1, wherein at least one pressure sensitive means (2, 3, 4) comprises at east one pressure sensitive plate of PVDF film.

3. The apparatus according to claim 1, wherein said at least one pressure sensitive means (2, 3, 4) comprises at least one pressure sensitive plate of PVDF film in combination with at least one electrostatic plate.

4. The apparatus according to claim 1, wherein said alarm device (14) is adapted to generate an audio signal.

5. The apparatus according to claim 1, wherein alarm device (14) is adapted to generate a light signal.

6. The apparatus according to claim 1, wherein said alarm device (14) is adapted to generate an audio signal and a light signal.

7. The apparatus according to claim 1, wherein said at least one pressure sensitive means (2, 3, 4) is installed in at least one of a seat, a back rest, and a safety belt.

8. The apparatus of claim 7, further comprising plural pressure sensitive means positioned to contact plural portions of said person's body.

9. A method of monitoring and estimating a person's wakefulness and, thereby, drowsiness, comprising the steps of:

generating an electric signal in response to said person's body movements relative to at least one stationary pressure sensitive means which contacts at least a portion of said person's body;

separating said electric signal into signals corresponding to duration and magnitude of true body movements, amplitude of heartbeat-related body movements as a function of heart rate, and amplitude of respiration-related body movements as a function of respiration rate;

measuring and comparing the duration and magnitude of the true body movements and the time-interval between the true body movements with previously measured corresponding values to determine possible changes;

measuring and comparing the amplitude of every heartbeat and respiration-related body movement and the time-interval between at least two successive heartbeats and respirations with previously measured corresponding values to determine possible changes;

correlating heartbeat and respiration-related changes with true body movement changes to establish a resulting change;

comparing the resulting change with a preset wakefulness threshold; and triggering an alarm when the threshold is reached as an indication of a reduced degree of wakefulness.

10. The method of claim 9, wherein said pressure sensitive means of said step of generating an electric signal in response to said person's body movements, is adapted for generating said electric signal while said person's body is in an upright position.

11. A method of monitoring a person's wakefulness, comprising the steps of:

locating a person's body adjacent plural, stationary, pressure-sensitive sensors;

generating an electric signal with said plural sensors responsive to body movements of said person;

separating said electric signal into plural signals corresponding to duration and magnitude of body movements, amplitude of heartbeat-related body movements, and amplitude of respiration-related body movements;

measuring and comparing the duration and magnitude of the body movements and the time-interval between the body movements with previously measured corresponding values to determine possible changes;

measuring and comparing the amplitude of every heartbeat and respiration-related body movement and the time-interval between at least two successive heartbeats and respirations with previously measured corresponding values to determine possible changes;

correlating heartbeat and respiration-related changes with body movement changes to establish a resulting change; and establishing a degree of wakefulness based on said resulting change.

12. The method of claim 11, wherein the step of separating said electric signal into the amplitude of heartbeat-related body movements and the amplitude of respiration-related body movements is performed as a function of heart rate and respiration rate respectively.

13. The method of claim 11, wherein said step of generating an electric signal with said plural sensors responsive to body movement of said person utilizes plural sensors comprising a PVDF film sensor and an electrostatic plate sensor monitoring different portions of said person's body.

14. The method of claim 11, further comprising a step of triggering an alarm upon said step of establishing a degree of wakefulness based on said resulting change, establishing a degree of wakefulness below a threshold value.

* * * * *